United States Patent
Kim et al.

(10) Patent No.: US 9,654,746 B2
(45) Date of Patent: May 16, 2017

(54) COLOUR LIGHTING CONTROL METHOD FOR IMPROVING IMAGE QUALITY IN A VISION SYSTEM

(71) Applicant: KOREA INSTITUTE OF INDUSTRIAL TECHNOLOGY, Cheonan-si, Chungcheongnam-do (KR)

(72) Inventors: Hyung Tae Kim, Cheonan-si (KR); Seung Taek Kim, Cheonan-si (KR)

(73) Assignee: KOREA INSTITUTE OF INDUSTRIAL TECHNOLOGY, Cheonan-si, Chungcheongnam-Do (KR)

( * ) Notice: Subject to any disclaimer, the term of this patent is extended or adjusted under 35 U.S.C. 154(b) by 403 days.

(21) Appl. No.: 14/353,781

(22) PCT Filed: Oct. 26, 2012

(86) PCT No.: PCT/KR2012/008844
§ 371 (c)(1),
(2) Date: Apr. 24, 2014

(87) PCT Pub. No.: WO2013/062345
PCT Pub. Date: May 2, 2013

(65) Prior Publication Data
US 2014/0300780 A1    Oct. 9, 2014

(30) Foreign Application Priority Data

Oct. 28, 2011    (KR) .................. 10-2011-0110960

(51) Int. Cl.
*G06K 9/00*    (2006.01)
*H04N 9/07*    (2006.01)
(Continued)

(52) U.S. Cl.
CPC ............ *H04N 9/07* (2013.01); *G01N 21/8806* (2013.01); *G01N 21/9501* (2013.01); *H04N 5/2354* (2013.01)

(58) Field of Classification Search
None
See application file for complete search history.

(56) References Cited

U.S. PATENT DOCUMENTS 6,304,294 B1 *  10/2001  Tao .......................... H04N 9/73
                                                         348/370
9,160,983 B2 *  10/2015  Kim ........................ H04N 7/18
(Continued)

FOREIGN PATENT DOCUMENTS

JP    06-058729 A    3/1994
JP    11-054289 A    2/1999
(Continued)

*Primary Examiner* — Andrae S Allison
(74) *Attorney, Agent, or Firm* — Revolution IP, PLLC (57) ABSTRACT

Provided is a color lighting control method including a lighting device having a plurality of lighting unit, the method including the steps of: (a) applying predetermined input voltages to the plurality of lighting units respectively and obtaining image data through the camera; (b) calculating an image histogram that is a distribution graph for displaying the number of pixels corresponding to each monochrome level intensity through the image data; (c) calculating a standard deviation of the image histogram; and (d) calculating an optimal input voltage value for each of the plurality of lighting units within an adjustment range of the predetermined input voltages, wherein the optimal input voltage value maximizes the standard deviation.

15 Claims, 5 Drawing Sheets

(51) Int. Cl.
*G01N 21/88* (2006.01)
*G01N 21/95* (2006.01)
*H04N 5/235* (2006.01)

(56) References Cited

U.S. PATENT DOCUMENTS

| | | | | |
|---|---|---|---|---|
| 2005/0218325 | A1* | 10/2005 | Nishiyama | H01J 37/026 250/311 |
| 2008/0267489 | A1* | 10/2008 | Xiao | G06T 7/001 382/147 |
| 2009/0272725 | A1* | 11/2009 | Kawazoe | B23K 26/032 219/121.64 |
| 2011/0051130 | A1* | 3/2011 | Kawahara | G01N 21/94 356/237.3 |
| 2013/0248705 | A1* | 9/2013 | Hayashi | H01J 37/02 250/307 |
| 2014/0226001 | A1* | 8/2014 | Kim | H05B 33/086 348/78 |

FOREIGN PATENT DOCUMENTS

| | | | |
|---|---|---|---|
| JP | 2000-037080 | * | 2/2000 |
| JP | 2001-229381 A | | 8/2001 |
| JP | 2003-256814 | * | 9/2003 |
| JP | 2007-226334 A | | 9/2007 |
| KR | 10-2006-0027225 A | | 3/2006 |

* cited by examiner

COLOUR LIGHTING CONTROL METHOD FOR IMPROVING IMAGE QUALITY IN A VISION SYSTEM

CROSS REFERENCE TO PRIOR APPLICATIONS

This application is a National Stage Application of PCT International Patent Application No. PCT/KR2012/008844 filed on Oct. 26, 2012, under 35 U.S.C. §371, which claims priority to Korean Patent Application No. 10-2011-0110960 filed on Oct. 28, 2011, which are all hereby incorporated by reference in their entirety.

TECHNICAL FIELD

The present invention relates to a color lighting control method for improving image quality of a vision system, and more particularly, to a color lighting control method in which color light is irradiated to an inspection subject to maximize the quality of an image shot by a camera and optimal color lighting conditions for obtaining such a high-quality image are rapidly and correctly set, thereby enabling a processing system to rapidly and correctly determine the quality of the inspection subject by reading an image collected by a vision system provided with a monochrome camera.

BACKGROUND ART

In general, a vision system is provided to inspection equipment developed to automatically, rapidly and correctly perform various visual inspections on an outward appearance of an inspection subject, which have depended on human eyesight, so as to shoot and collect digital images of the inspection subject and transfer the collected images to a processing system having a quality determining function.

Such a vision system is provided with a lighting device for irradiating predetermined light to an inspection subject and a camera for photographing the inspection subject to generate a digital image. Here, instead of a high-priced color camera, a monochrome camera is typically used as the camera.

The lighting device may be a monochromatic lighting device. However, as disclosed in Korean Patent Application Laid-open Publication No. 2006-0027225, controllable color lighting has recently been widely applied to vision systems such as outward appearance inspection equipment for an LCD in order to more effectively detect a surface defect of an inspection subject.

However, a correlation between the quality of a monochromatic image shot by a monochrome camera and color lighting conditions is not clear. Therefore, an operator should manually find and set optimal color lighting conditions. However, this method is not only complex but also subjective since whether found lighting conditions are optimal is determined depending on eyesight of the operator. Moreover, whenever inspection subjects are changed, such a complex setting operation should be performed again, causing inconvenience to the operator.

When various types of inspection subjects are inspected, an additional vision system may be provided for each inspection subject in order to resolve the above-mentioned inconvenience, but this method increases the cost of inspection equipment.

Therefore, in the field of a vision system to which color lighting is applied, it is an important issue to develop an optimal color lighting control method for maximizing the quality of an image shot by a monochrome camera of a vision system so that a processing system rapidly and correctly determines the quality of an inspection subject by reading the image.

Korean Patent Application Laid-open Publication No. 2011-0060194 discloses a color lighting control method in which each pair of images corresponding to 256 to the power of 3 ($256^3$) is obtained and analyzed while gradually adjusting each color brightness of RGB color lighting, thereby finding optimal color lighting conditions.

However, this conventional color lighting control method merely achieves improvement with respect to automatic acquisition and analysis of an image, but requires a large amount of images to be acquired and analyzed. Therefore, it takes a long time to find optimal color lighting conditions, and the life of a detector of a camera is shortened due to shooting of a large amount of images.

According to the conventional color lighting control method, an optimal image is determined according to which one of images A and B that have different color lighting conditions has a larger contrast difference between an inspection region and a background region. However, in the case where a plurality of inspection regions exist, the image A may have a larger contrast difference with respect to some inspection regions, but the image B may have a larger contrast difference with respect to other inspection regions. Therefore, it may be difficult to determine an optimal image if two images which have different color lighting conditions have conflicting superiority with respect to contrast.

In order to overcome such a limitation, the contrast difference may be checked on the basis of a specific inspection region from among a plurality of inspection regions so as to determine an optimal image. However, in this case, since the optimal image is not determined in consideration of all inspection regions, the reliability of the determination is relatively low.

That is, according to the conventional color lighting control method, a criterion for determining an optimal image is ambiguous, and thus, the method is not reliable even though optimal color lighting conditions may be found.

DISCLOSURE OF THE INVENTION

Technical Problem

In order to overcome the above-mentioned problems, the present invention provides a color lighting control method for improving image quality of a vision system, according to which a criterion on an image having optimal quality may be clearly digitized and optimal color lighting conditions for obtaining a high-quality image may be rapidly and correctly set, when the optimal color lighting conditions for maximizing the quality of an image shot by a camera while irradiating color light to an inspection subject are derived.

Technical Solution

A color lighting control method for improving image quality of a vision system including a lighting device having a plurality of lighting units for irradiating lights of different wavelengths to an inspection subject and a lighting control unit for controlling a light irradiation intensity by respectively adjusting input voltages applied to the lighting units and a camera for shooting an image of the inspection subject to generate a monochrome digital image, according to an embodiment of the present invention includes the steps of:

(a) applying predetermined input voltages to the plurality of lighting units respectively; (b) obtaining image data through the camera; (c) calculating an image histogram that is a distribution graph for displaying the number of pixels corresponding to each monochrome level intensity through the image data; (d) calculating a standard deviation of the image histogram; and (e) calculating an optimal input voltage value for each of the plurality of lighting units within an adjustment range of the predetermined input voltages, wherein the optimal input voltage value maximizes the standard deviation.

In the step (e), an input voltage value that maximizes the standard deviation, from among input voltage values obtained through repetition of the steps (b), (c) and (d) while applying a plurality of input voltages adjusted at a predetermined interval to the plurality of lighting units respectively, may be calculated as the optimal input voltage value.

In the step (e), the optimal input voltage value that maximizes the standard deviation may be calculated through a steepest decent method in which an operation of calculating an amount of change of the standard deviation according to an input voltage change and applying the input voltage adjusted in consideration of the calculated change amount is repeated.

In the step (e), the optimal input voltage value that maximizes the standard deviation may be calculated through a golden section search method in which an operation of applying a plurality of input voltages adjusted at a predetermined first interval to the plurality of lighting units respectively, re-applying the plurality of input voltages adjusted to be increased or decreased by a second interval smaller than the first interval with respect to the input voltage that maximizes the standard deviation, and calculating the standard deviation for each input voltage is repeated at least once.

A color lighting control method for improving image quality of a vision system including a lighting device having a plurality of lighting units for irradiating lights of different wavelengths to an inspection subject and a lighting control unit for controlling a light irradiation intensity by respectively adjusting input voltages applied to the lighting units and a camera for shooting an image of the inspection subject to generate a monochrome digital image, according to another embodiment of the present invention, includes the steps of: (a') applying predetermined input voltages to the plurality of lighting units respectively; (b') obtaining image data through the camera; (c') calculating an image histogram that is a distribution graph for displaying the number of pixels corresponding to each monochrome level intensity through the image data; (d') calculating a maximum value of the image histogram; and (e') calculating an optimal input voltage value for each of the plurality of lighting units within an adjustment range of the predetermined input voltages, wherein the optimal input voltage value maximizes the maximum value.

In the step (d'), the maximum value may be calculated within bottom 85-95% of the entire range of the monochrome level intensity.

In the step (d'), the maximum value may be calculated within top 85-95% of the entire range of the monochrome level intensity.

In the step (d'), the maximum value may be calculated within middle 70-90% of the entire range of the monochrome level intensity excluding top 5-15% and bottom 5-15% thereof.

In the step (e'), an input voltage value that maximizes the maximum value, from among input voltage values obtained through repetition of the steps (b'), (c') and (d') while applying a plurality of input voltages adjusted at a predetermined interval to the plurality of lighting units respectively, may be calculated as the optimal input voltage value.

In the step (e'), the optimal input voltage value that maximizes the maximum value may be calculated through a steepest decent method in which an operation of calculating an amount of change of the standard deviation according to an input voltage change and applying the input voltage adjusted in consideration of the calculated change amount is repeated.

In the step (e'), the optimal input voltage value that maximizes the maximum value may be calculated through a golden section search method in which an operation of applying a plurality of input voltages adjusted at a predetermined first interval to the plurality of lighting units respectively, re-applying the plurality of input voltages adjusted to be increased or decreased by a second interval smaller than the first interval with respect to the input voltage that maximizes the maximum value, and calculating the standard deviation for each input voltage is repeated at least once.

Advantageous Effects

According to the color lighting control method for improving image quality of a vision system of the present invention, an image histogram that is a distribution graph for displaying the number of pixels corresponding to each monochrome level intensity is calculated through image data obtained from a camera, and color lighting conditions that maximize a standard deviation or maximum value of the image histogram are detected, and thus, optimal color lighting conditions for obtaining a high-quality image may be clearly and rapidly derived.

That is, when the optimal color lighting conditions are derived, a criterion on an image having optimal quality is clearly digitized as a state where the standard deviation or maximum value of the image histogram is largest, so as to clearly and rapidly derive the optimal color lighting conditions, thereby maximizing the quality of the image obtained from the camera.

Furthermore, in the case where the optimal color lighting conditions are derived according to whether an image has a largest maximum value of the image histogram, the maximum value is calculated within bottom 85-95% of the entire range of monochrome level intensity excluding top 5-15% thereof, thereby preventing an error on determination of the optimal color lighting conditions due to a hot pixel of the camera or pixel saturation caused by a highly-reflective metal part of an inspection subject.

Similarly, the maximum value is calculated within top 85-95% of the entire range of monochrome level intensity excluding bottom 5-15% thereof, thereby preventing an error on determination of the optimal color lighting conditions due to a dark area of an image which occurs when an image-shooting area of the camera is larger than an irradiation area of color lighting.

Furthermore, a steepest decent method or golden section search method is used to detect the color lighting conditions that maximize the standard deviation or maximum value of the image histogram. Therefore, the number of times of shooting images by the camera is remarkably reduced, and thus, operations required for detecting the optimal color lighting conditions may be reduced and a life of a camera detector may be prevented from being shortened.

MODE FOR CARRYING OUT THE INVENTION

Hereinafter, embodiments of the present invention will be described in detail with reference to the accompanying drawings so that the present invention is easily carried out by a person of ordinary skill in the technical field to which the present invention belongs (hereinafter, referred to as "a person skilled in the art"). However, the present invention may be implemented in various different forms and should not be construed as being limited to the embodiments described herein.

A color lighting control method for improving image quality of a vision system (hereinafter, referred to as a "color lighting control method") according to the present invention is applied to a vision system, which has a function of shooting and collecting digital images of inspection subjects such as a wafer and a semiconductor chip and is provided to inspection equipment developed to automatically, rapidly and correctly perform various visual inspections on outward appearances of the inspection subjects, so as to check the qualities of the images according to a clearly digitized criterion and derive optimal color lighting conditions in order to maximize the qualities of the images shot by a camera.

Figure 1:
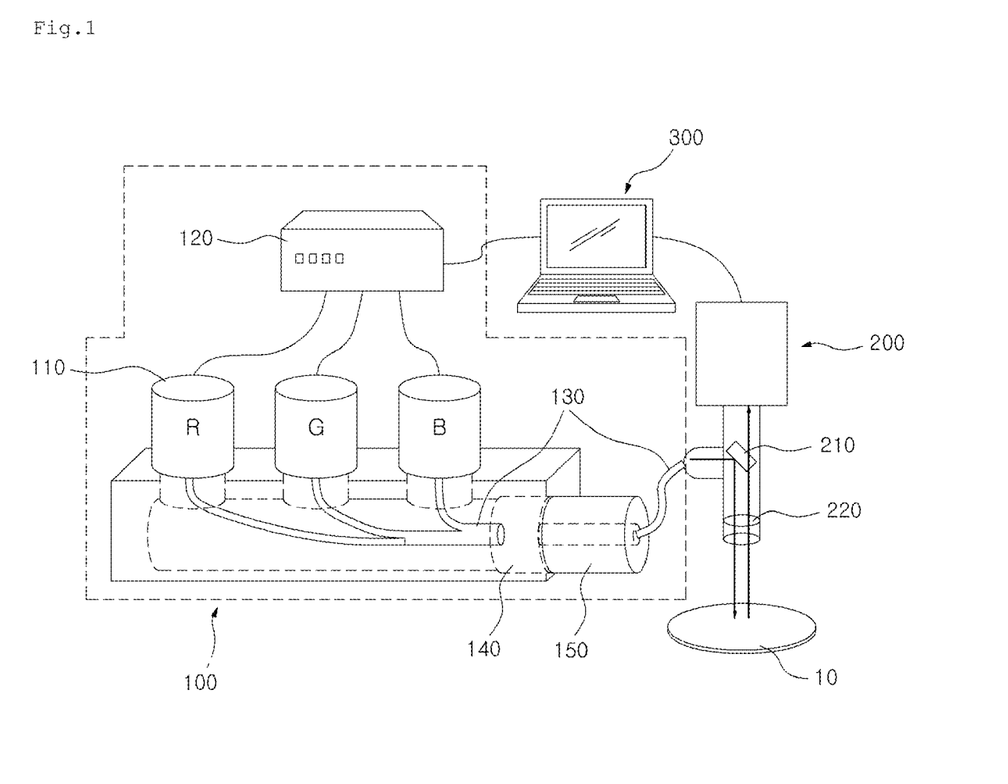
FIG. 1 is a schematic diagram illustrating a vision system for implementing a color lighting control method for improving image quality of a vision system according to the present invention.

Hereinafter, a vision system of inspection equipment to which the color lighting control method according to the present invention is applied will be described with reference to FIG. 1.

The vision system, which serves to shoot and collect a digital image of an inspection subject and transfer the digital image to a processing system having a quality determining function, is roughly divided into a lighting device 100, a camera 200 and a control system 300.

The lighting device 100 irradiates light to an inspection subject 10 so that the camera 200 obtains an image of the inspection subject 10. The lighting device 100 may include a plurality of lighting units 110 for irradiating light of different wavelengths, an amplifier 120, an optical fiber 130, a mixer unit 140, and a connection unit 150.

The plurality of lighting units 110 of the vision system to which the present invention is applied are implemented with LED lighting devices that respectively emit the three primary light, i.e., red (R), green (G) and blue (B) light, but the implementation method is not limited thereto. For example, the plurality of lighting units 110 may include two LED lighting devices that emit light of different wavelengths, or may include four or more LED lighting devices including an LED for emitting white (W) light.

The amplifier 120, which is arranged between the plurality of lighting units 110 and the control system 300 for controlling input to the lighting unit 110, serves to amplifier a signal of the control system 300. The optical fiber 130 transfers the light irradiated by the plurality of lighting units 110 or light synthesized by the mixer unit 140.

The mixer unit 140 is provided in the shape of a chamber where the light irradiated by the plurality of lighting units 110 is synthesized. The connection unit 150 connects the optical fibers 130 respectively connected to the mixer unit 140 and the camera 200 so that the light synthesized in the mixer unit 140 is transferred to the camera 200.

However, the above-described detailed configuration of the lighting device 100 is merely an example, and thus, the lighting device 100 may be configured in different ways.

The camera 200 is provided with a plurality of pixels for detecting light so as to convert reflected light of the inspection subject into a digital image. In general, an inexpensive monochrome camera is provided as the camera 200.

A monochrome level I(x,y) that is a digital value of each pixel of the camera 200 is calculated by the control system 300, and result values of the calculation are collected so as to produce an image histogram. Here, since the monochrome level I(x,y) relates to an intensity of light incident to a pixel, the following equation is satisfied.

$$I(x,y)=f(\rho(x,y)),$$

($\rho$: intensity of light sensed by a camera pixel)

A light wavelength characteristic E of a lighting device is expressed as the following equation, provided that a plurality of lighting devices are used and light output of each lighting device is changed by a predetermined lighting circuit according to input voltages $V_1$-$V_1$ of the lighting devices.

$$\vec{E}(\lambda) = \vec{E}(\lambda, 1, \ldots, V_l) = \sum_{j=1}^{l} \vec{E}(\lambda, V_j) \quad (\lambda: \text{wavelength})$$

$\rho$ is redefined by this equation as below $$\rho(x,y)=C\int_0^\infty R(\lambda)S(x,y,\lambda)\vec{E}(\lambda)d\lambda$$

(C: arbitrary constant, R: light sensing characteristic of a camera, S: light reflection characteristic of an inspection subject)

That is, the lighting conditions are adjusted by the input voltages $V_1$-$V_1$ of each lighting device, and the digital image by the camera 200 is generated by gathering I(x,y), wherein I(x,y) is image data for the image.

A half mirror 210 reflects synthesized light transferred through the optical fiber 130 so as to coaxially irradiate the reflected light to the inspection subject 10, and allows light reflected from the inspection subject 10 to pass the half mirror and travel to the camera 200.

An optical instrument 220 is arranged between the half mirror 210 and the inspection subject 10, so as to allow the synthesized light transferred through the optical fiber 130 to be widely and uniformly irradiated to the inspection subject 10 and allow the light reflected from the inspection subject 10 to be concentrated and travel to the camera 200.

The control system 300 receives image data for the monochrome level I(x,y) from the camera so as to calculate an image histogram that is a distribution graph for displaying the number of pixels corresponding to each monochrome level intensity by using the following equation.

$$z_i | H | I_i \leq I(x,y) \leq I_{i+1} \text{ for } \forall x, \forall y$$

(i: specific monochrome level, for an 8-bit image, i=1-256, z: the number of pixels belonging to the monochrome level, H: a set of pixels belonging to the monochrome level)

Here, $z_i$ may be expressed as $z(I_i)$, the image histogram is changed by the input voltages $V_1$-$V_1$ to the plurality of lighting devices 100.

The control system 300 calculates a standard deviation or maximum value of the image histogram calculated for a specific image. The standard deviation of the image histogram, i.e., $\sigma_z^2$, may be calculated by the following equation.

$$\sigma_z^2 = \frac{1}{n} \sum_i z_i^2 - \bar{z}^2$$

(average of the image histogram)

$$\bar{z} = \frac{1}{n} \sum_i^n z_i$$

The control system 300 compares the standard deviation or maximum value with standard deviations or maximum values of image histograms calculated for other images so as to detect input voltages $V_1$-$V_1$ of an image histogram of which the standard deviation or maximum value is largest.

The fact that the standard deviation of the image histogram of a specific image from among images obtained under various color lighting conditions is maximal indicates that a difference between the number of pixels corresponding to each monochrome level intensity and the average pixel number of all monochrome levels is large, which means that monochrome levels of pixels are not concentrated on a specific value but are widely distributed.

That is, the fact that the standard deviation of the image histogram is maximal may indicate that a monochrome level difference of each pixel is maximized, thereby averagely maximizing discrimination between an inspection region and a background region.

The fact that the maximum value of the image histogram of a specific image from among images obtained under various color lighting conditions is largest indicates that the number of pixels showing a specific monochrome level intensity is largest, which means that a portion having generally uniform monochrome level intensities, such as an inspection region, is maximized, thereby enabling easiest discrimination between the inspection region and a background region.

Therefore, an image having a largest standard deviation or maximum value of an image histogram may be an optimal high-quality image that enables easiest reading of an inspection region, and the input voltages $V_1$-$V_1$ to the plurality of lighting units 110 for this state, detected by the control system 300, may be optimal color lighting conditions.

However, in the case where the optimal color lighting conditions are determined according to whether an image has a largest maximum value of an image histogram, it is preferable that the maximum value is calculated within bottom 85-95% of the entire range of monochrome level intensity excluding top 5-15% thereof. This is for preventing an error on determination of the optimal color lighting conditions due to a hot pixel of a camera or pixel saturation caused by a highly-reflective metal part of an inspection subject.

Similarly, it is preferable that the maximum value is calculated within top 85-95% of the entire range of monochrome level intensity excluding bottom 5-15% thereof. This is for preventing an error on determination of the optimal color lighting conditions due to a dark area of an image which occurs when an image-shooting area of a camera is larger than an irradiation area of color lighting.

Figure 3:
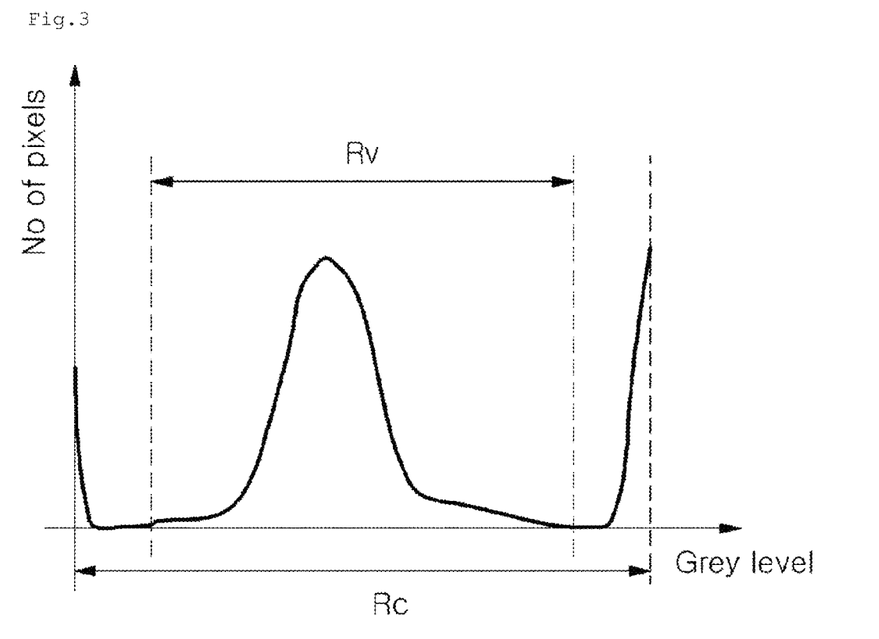
FIG. 3 is an image histogram calculated from image data according to a color lighting control method for improving image quality of a vision system according to an embodiment of the present invention.

Therefore, it may be most preferable that the maximum value is calculated within an effective range $R_v$ of monochrome level intensity, i.e., middle 70-90% of the entire range $R_c$ of monochrome level intensity excluding top 5-15% and bottom 5-15% thereof, as illustrated in FIG. 3. It may be most preferable that the color lighting conditions obtained when the maximum value is largest are determined as the optimal color lighting conditions.

Here, if the excluded range is lower than 5%, the above-mentioned hot pixel, saturated pixel and dark pixel may not be effectively prevented, and, if the excluded range is higher than 15%, valid data may be excluded since the excluded range is excessive. Therefore, it may be preferable that top 5-15% and bottom 5-15% of the entire range of monochrome level intensity are excluded.

Various methods may be used for the control system 300 to compare standard deviations or maximum values of image histograms in order to detect the input voltages $V_1$-$V_1$ (optimal input voltage values) of an image histogram of which the standard deviation or maximum value is largest.

According to a relatively simple method of detecting the optimal input voltage values, combinations of input voltages adjusted at a predetermined interval are applied to the plurality of lighting units 110 in order to calculate standard deviations or maximum values of image histograms of respective cases, and then, the standard deviations or maximum values of the image histograms are compared with each other so that input voltage values that induce a largest standard deviation or maximum value are calculated as the optimal input voltage values.

For example, in the case where an adjustment range of an input voltage is 0-5 V, input voltages to the R, G and B lighting units 110 are adjusted at an interval of 0.156 V and are combined so as to obtain a plurality pieces of image data, and standard deviations or maximum values of image histograms for the pieces of images data are compared with each other so that input voltage values that induce a largest standard deviation or maximum value are calculated as the optimal input voltage values.

As another method of detecting the optimal input voltage values, a steepest decent method may be used so that an operation of calculating amounts of changes of standard deviations or maximum values according to changes of input voltage and applying the input voltages re-adjusted in consideration of the calculated change amounts is repeatedly performed.

According to this method, amounts of changes of standard deviations or maximum values of image histograms for two or more pieces of image data are calculated. On the basis of the fact that the change amounts become 0 at peak points, the input voltages are applied after being re-adjusted by a predetermined amount so that the change amounts approximate 0, and the foregoing operation is repeated to thereby detect peak points where the standard deviations or maximum values are largest.

Furthermore, as another method of detecting the optimal voltage values, a golden section search method may be used. According to this method, a plurality of input voltages adjusted at a predetermined first interval are applied to the plurality of lighting units respectively, and the plurality of input voltages adjusted to be increased or decreased by a second interval smaller than the first interval with respect to an input voltage having a largest standard deviation or maximum value are re-applied to the plurality of lighting units so as to calculate standard deviations and maximum values for each input voltage, and this operation is performed at least once.

For example, in the case where an adjustment range of an input voltage is 0-5 V, input voltages to the R, G and B lighting units 110 are adjusted at a wide interval of 0.5 V (first interval) and are combined so as to obtain a plurality pieces of image data, and standard deviations or maximum values of image histograms for the pieces of images data are compared with each other so that input voltage values that induce a largest standard deviation or maximum value are calculated, and then, with respect to the calculated input voltage values, the input voltages to the R, G and B lighting units 110 are adjusted to be increased or decreased by a narrow interval of 0.156 V (second interval) within a range of 1 V so as to obtain a plurality of pieces of image data and compare standard deviations or maximum values of image histograms for the obtained pieces of image data so that input voltage values that induce a largest standard deviation or maximum value are calculated as the optimal input voltages.

In the case where such a steepest decent method or golden section search method is used, the number of times of obtaining image data and image histograms for deriving the optimal color lighting conditions may be reduced, and thus, the operation of deriving the optimal color lighting conditions may be more rapidly performed.

Besides the above-mentioned methods, other various mathematical methods may be used for the control system 300 to calculate a standard deviation or maximum value of an image histogram.

Hereinafter, a color lighting control method performed by the above-described vision system, according to an embodiment of the present invention, will be described with reference to FIGS. 2 to 8.

Figure 2:
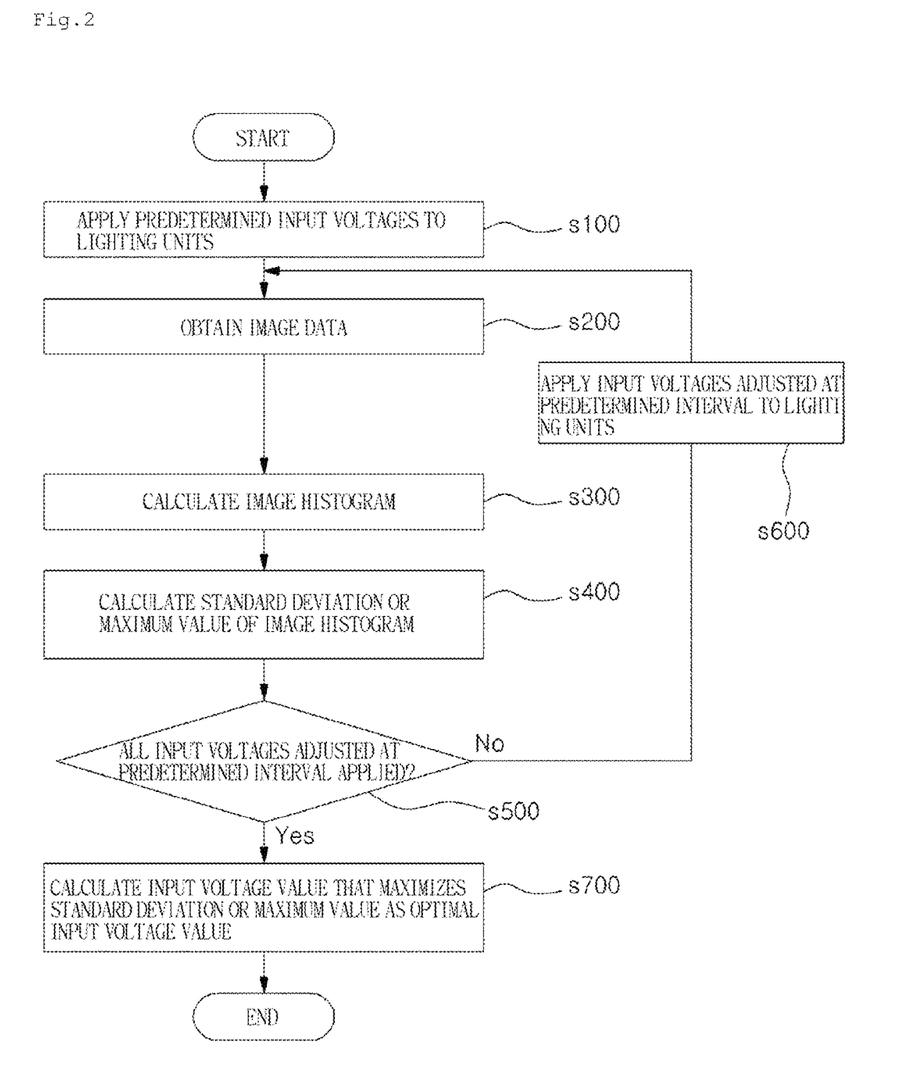
FIG. 2 is a flowchart illustrating a color lighting control method for improving image quality of a vision system according to an embodiment of the present invention.

According to the color lighting control method according to an embodiment of the present invention, in order to calculate the optimal color lighting conditions, combinations of input voltages adjusted at a predetermined interval are applied to the plurality of lighting units 110 in order to calculate standard deviations or maximum values of image histograms of respective cases, and then, the standard deviations or maximum values of the image histograms are compared with each other so that input voltage values that induce a largest standard deviation or maximum value are determined as the optimal input voltage values.

The control system 300 applies predetermined input voltages to the plurality of lighting units 110 so that arbitrary synthesized light is irradiated to the inspection subject 10 (s100).

Then, the camera 200 obtains image data obtained under the synthesized light irradiation condition and transfers the image data to the control system 300 (s200), and the control system 300 calculates an image histogram for the image data through the above-described equations (s300).

Thereafter, the control system 300 calculates a standard deviation or maximum value of the calculated image histogram (s400).

Thereafter, the control system 300 applies all combinations of input voltages adjusted at a predetermined interval so as to check whether the standard deviation or maximum value of the image histogram has been calculated (s500). If another combination of input voltages has not been applied yet, the control system 300 applies another combination of input voltages adjusted at a predetermined interval to the plurality of lighting units 110 (s600).

The above-described image data acquisition (s200), image histogram calculation (s300), and calculation of the standard deviation or maximum value of the image histogram (s400) are repeatedly performed.

In the case where a standard deviation or maximum value of each image histogram is calculated by applying all combinations of input voltages as described above, input voltage values that induce a largest standard deviation or maximum value among all calculated standard deviations or maximum values are calculated as optimal input voltage values (optimal input voltage conditions) (s700).

Thereafter, an inspection is performed while applying input voltages according to the calculated optimal input voltage conditions to the plurality of lighting units 110, so that the processing system of the inspection equipment rapidly and correctly determines a quality on the basis of an optimal high-quality image.

Figure 4:
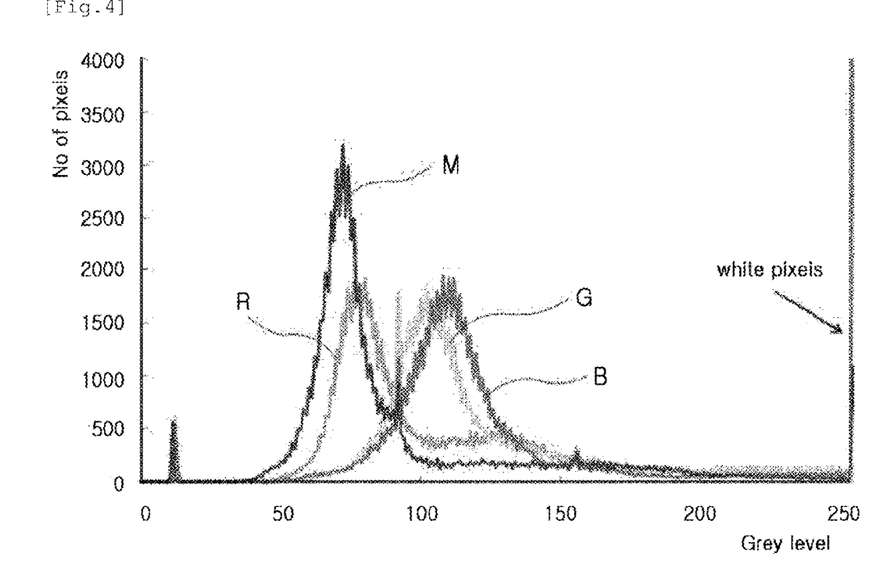
FIG. 4 is a graph illustrating an image histogram obtained by virtue of synthesized light according to optimal color lighting conditions derived by a color lighting control method for improving image quality of a vision system according to an embodiment of the present invention and image histograms obtained under monochrome lighting of red, green and blue colors.

FIG. 4 is a graph illustrating an image histogram M obtained by virtue of synthesized light according to the optimal color lighting conditions derived by the color lighting control method of the present invention and image histograms R, G and B obtained under monochrome lighting of red, green and blue colors.

As illustrated in FIG. 4, compared to the image histograms R, G and B, the image histogram M obtained by virtue of optimal synthesized light has a large maximum value at a specific monochrome level intensity and is relatively widely distributed. Therefore, contrast distribution is increased and an image is more sharpened, thereby enabling easier determination of quality.

Figure 5:
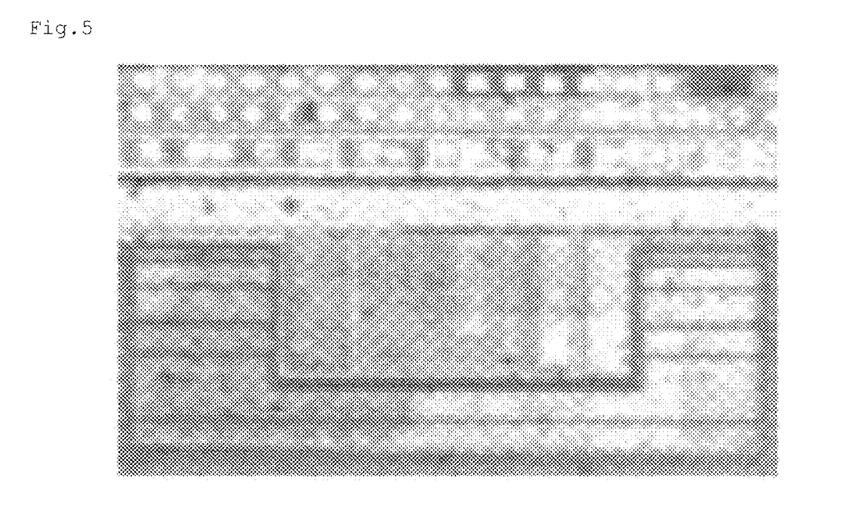
FIGS. 5 to 7 are images to which monochrome lighting of R, G and B is applied.
Figure 6:
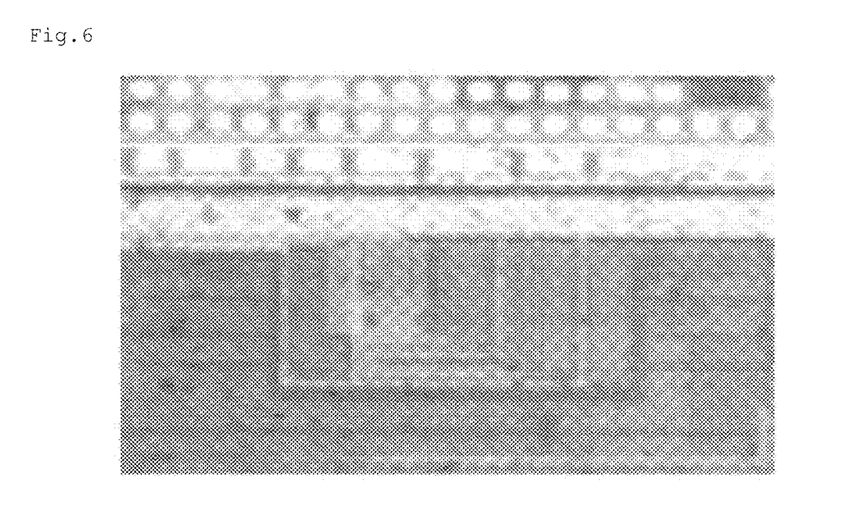
Figure 7:
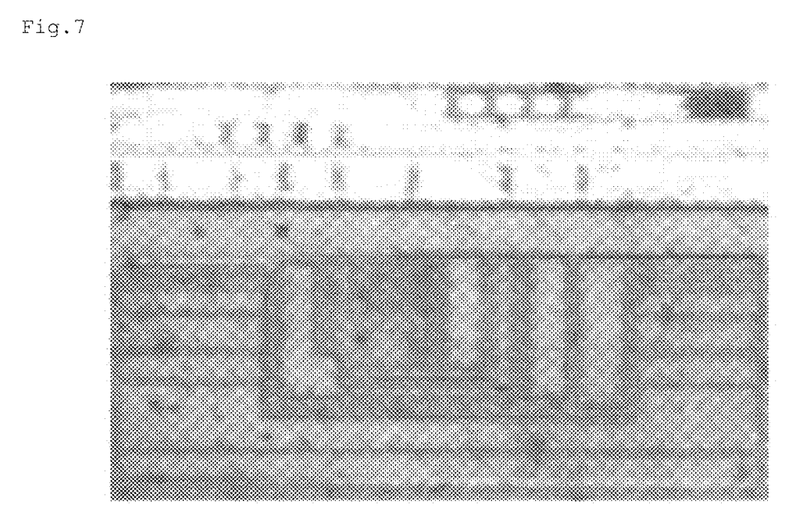
Figure 8:
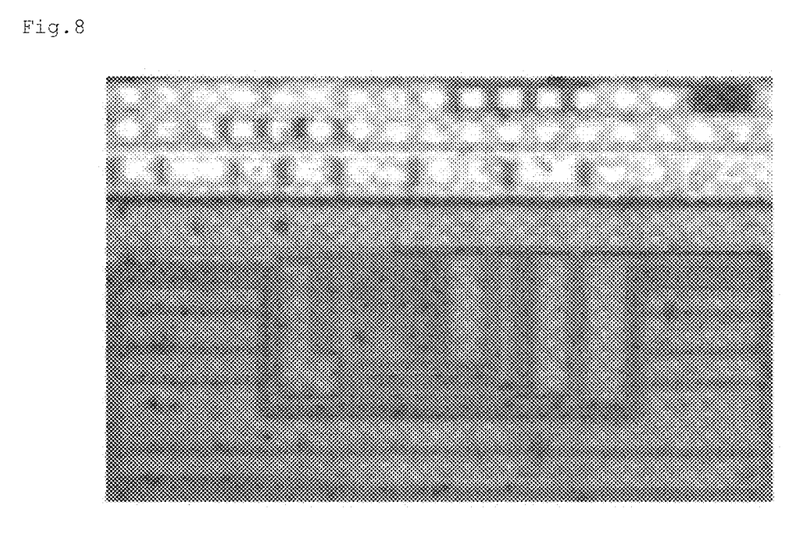
FIG. 8 is an image to which optimal color lighting conditions derived by a color lighting control method for improving image quality of a vision system according to an embodiment of the present invention are applied.

FIGS. 5 to 7 are actual images to which monochrome lighting is applied, and FIG. 8 is an actual image to which the optimal color lighting conditions derived by the color lighting control method of the present invention are applied. It may be understood that in the case where the optimal color lighting conditions derived by the color lighting control method of the present invention are applied, details of elements are easily identified with eyes.

According to the color lighting control method according to an embodiment of the present invention, in order to calculate the optimal color lighting conditions, combinations of input voltages adjusted at a predetermined interval are applied to the plurality of lighting units 110 in order to calculate standard deviations or maximum values of image histograms of respective cases, and then, the standard deviations or maximum values of the image histograms are compared with each other so that input voltage values that induce a largest standard deviation or maximum value are determined as the optimal input voltage values. However, the method of calculating the optimal color lighting conditions is not limited thereto, and thus, the above-mentioned steepest decent method or golden search method may be used.

Although it has been described that a standard deviation or maximum value of an image histogram is used as a reference for determining an optimal high-quality image, the color lighting control method according to the present invention is not limited thereto. Therefore, both the standard deviation and maximum value may be used as references so that the standard deviation is auxiliary used when the optimal color lighting conditions are not clearly determined by the maximum value.

While the present invention has been described with respect to the specific embodiments, it will be apparent to those skilled in the art that various changes and modifications may be made without departing from the spirit and scope of the invention as defined in the following claims.

INDUSTRIAL APPLICABILITY

To be used in the industry, the present invention provides a color lighting control method for improving image quality of a vision system, and more particularly, a color lighting control method in which color light is irradiated to an inspection subject to maximize the quality of an image shot by a camera and optimal color lighting conditions for obtaining such a high-quality image are rapidly and correctly set, thereby enabling a processing system to rapidly and correctly determine the quality of the inspection subject by reading an image collected by a vision system provided with a monochrome camera.

The invention claimed is:

1. A color lighting control method for improving image quality of a vision system comprising a lighting device having a plurality of lighting units for irradiating lights of different wavelengths to an inspection subject and a lighting control unit for controlling a light irradiation intensity by respectively adjusting input voltages applied to the lighting units and a camera for shooting an image of the inspection subject to generate a monochrome digital image, the method comprising the steps of:
(a) applying predetermined input voltages to the plurality of lighting units respectively;
(b) obtaining image data through the camera;
(c) calculating an image histogram that is a distribution graph for displaying the number of pixels corresponding to each monochrome level intensity through the image data;
(d) calculating a standard deviation of the image histogram; and
(e) calculating an optimal input voltage value for each of the plurality of lighting units within an adjustment range of the predetermined input voltages, wherein the optimal input voltage value maximizes the standard deviation, wherein the optimal input voltage value that maximizes the standard deviation is calculated through a steepest decent method in which an operation of calculating an amount of change of the standard deviation according to an input voltage change and applying the input voltage adjusted in consideration of the calculated change amount is repeated.

2. The color lighting control method of claim 1, wherein, in the step (e), an input voltage value that maximizes the standard deviation, from among input voltage values obtained through repetition of the steps (b), (c) and (d) while applying a plurality of input voltages adjusted at a predetermined interval to the plurality of lighting units respectively, is calculated as the optimal input voltage value.

3. The color lighting control method of claim 1, wherein, in the step (e), the optimal input voltage value that maximizes the standard deviation is calculated through a golden section search method in which an operation of applying a plurality of input voltages adjusted at a predetermined first interval to the plurality of lighting units respectively, re-applying the plurality of input voltages adjusted to be increased or decreased by a second interval smaller than the first interval with respect to the input voltage that maximizes the standard deviation, and calculating the standard deviation for each input voltage is repeated at least once.

4. A color lighting control method for improving image quality of a vision system comprising a lighting device having a plurality of lighting units for irradiating lights of different wavelengths to an inspection subject and a lighting control unit for controlling a light irradiation intensity by respectively adjusting input voltages applied to the lighting units and a camera for shooting an image of the inspection subject to generate a monochrome digital image, the method comprising the steps of:
(a') applying predetermined input voltages to the plurality of lighting units respectively;
(b') obtaining image data through the camera;
(c') calculating an image histogram that is a distribution graph for displaying the number of pixels corresponding to each monochrome level intensity through the image data;
(d') calculating a maximum value of the image histogram; and
(e') calculating an optimal input voltage value for each of the plurality of lighting units within an adjustment range of the predetermined input voltages, wherein the optimal input voltage value maximizes the maximum value, wherein the optimal input voltage value that maximizes the maximum value is calculated through a steepest decent method in which an operation of calculating an amount of change of the standard deviation according to an input voltage change and applying the input voltage adjusted in consideration of the calculated change amount is repeated.

5. The color lighting control method of claim 4, wherein, in the step (d'), the maximum value is calculated within bottom 85-95% of the entire range of the monochrome level intensity.

6. The color lighting control method of claim 5, wherein, in the step (e'), an input voltage value that maximizes the maximum value, from among input voltage values obtained through repetition of the steps (b'), (c') and (d') while applying a plurality of input voltages adjusted at a predetermined interval to the plurality of lighting units respectively, is calculated as the optimal input voltage value.

7. The color lighting control method of claim 5, wherein, in the step (e'), the optimal input voltage value that maximizes the maximum value is calculated through a golden section search method in which an operation of applying a plurality of input voltages adjusted at a predetermined first interval to the plurality of lighting units respectively, re-applying the plurality of input voltages adjusted to be increased or decreased by a second interval smaller than the first interval with respect to the input voltage that maximizes the maximum value, and calculating the standard deviation for each input voltage is repeated at least once.

8. The color lighting control method of claim 4, wherein, in the step (d'), the maximum value is calculated within top 85-95% of the entire range of the monochrome level intensity.

9. The color lighting control method of claim 8, wherein, in the step (e'), an input voltage value that maximizes the maximum value, from among input voltage values obtained through repetition of the steps (b'), (c') and (d') while applying a plurality of input voltages adjusted at a predetermined interval to the plurality of lighting units respectively, is calculated as the optimal input voltage value.

10. The color lighting control method of claim 8, wherein, in the step (e'), the optimal input voltage value that maximizes the maximum value is calculated through a golden section search method in which an operation of applying a plurality of input voltages adjusted at a predetermined first interval to the plurality of lighting units respectively, re-applying the plurality of input voltages adjusted to be increased or decreased by a second interval smaller than the first interval with respect to the input voltage that maximizes the maximum value, and calculating the standard deviation for each input voltage is repeated at least once.

11. The color lighting control method of claim 4, wherein, in the step (d'), the maximum value is calculated within middle 70-90% of the entire range of the monochrome level intensity excluding top 5-15% and bottom 5-15% thereof.

12. The color lighting control method of claim 11, wherein, in the step (e'), an input voltage value that maximizes the maximum value, from among input voltage values obtained through repetition of the steps (b'), (c') and (d') while applying a plurality of input voltages adjusted at a predetermined interval to the plurality of lighting units respectively, is calculated as the optimal input voltage value.

13. The color lighting control method of claim 11, wherein, in the step (e'), the optimal input voltage value that maximizes the maximum value is calculated through a golden section search method in which an operation of applying a plurality of input voltages adjusted at a predetermined first interval to the plurality of lighting units respectively, re-applying the plurality of input voltages adjusted to be increased or decreased by a second interval smaller than the first interval with respect to the input voltage that maximizes the maximum value, and calculating the standard deviation for each input voltage is repeated at least once.

14. The color lighting control method of claim 4, wherein, in the step (e'), an input voltage value that maximizes the maximum value, from among input voltage values obtained through repetition of the steps (b'), (c') and (d') while applying a plurality of input voltages adjusted at a predetermined interval to the plurality of lighting units respectively, is calculated as the optimal input voltage value.

15. The color lighting control method of claim 4, wherein, in the step (e'), the optimal input voltage value that maximizes the maximum value is calculated through a golden section search method in which an operation of applying a plurality of input voltages adjusted at a predetermined first interval to the plurality of lighting units respectively, re-applying the plurality of input voltages adjusted to be increased or decreased by a second interval smaller than the first interval with respect to the input voltage that maximizes the maximum value, and calculating the standard deviation for each input voltage is repeated at least once.

* * * * *